United States Patent [19]
Lappi et al.

[11] Patent Number: 6,114,832
[45] Date of Patent: Sep. 5, 2000

[54] CHARGING METHOD AND CHARGING ARRANGEMENT

[75] Inventors: Erkki Lappi, Klaukkala; Vesa-Pekka Torvinen, Oulu; Ilkka Heikkilä, Oulu; Arto Pietilä, Oulu, all of Finland

[73] Assignee: Polar Electro Oy, Kempele, Finland

[21] Appl. No.: 09/257,415

[22] Filed: Feb. 25, 1999

[30] Foreign Application Priority Data

Mar. 2, 1998 [FI] Finland ...................................... 980472

[51] Int. Cl.⁷ ....................................................... H02J 7/00
[52] U.S. Cl. ........................... 320/108; 600/301; 600/500
[58] Field of Search ............................. 320/108; 600/301, 600/560

[56] References Cited

U.S. PATENT DOCUMENTS

| | | |
|---|---|---|
| 4,527,096 | 7/1985 | Kindlmann . |
| 4,791,933 | 12/1988 | Asai et al. ................................ 600/387 |
| 5,600,225 | 2/1997 | Goto ........................................ 320/108 |
| 5,832,296 | 11/1998 | Wang et al. .............................. 395/823 |
| 5,907,281 | 5/1999 | Miller et al. ........................... 340/573.6 |
| 5,953,434 | 9/1999 | Boyden ................................... 381/376 |
| 5,975,204 | 11/1999 | Tubel et al. ......................... 166/250.15 |
| 5,977,913 | 11/1999 | Christ ..................................... 342/465 |

FOREIGN PATENT DOCUMENTS 196 49 682  6/1998  Germany .

Primary Examiner—Peter S. Wong
Assistant Examiner—Pia Tibbits
Attorney, Agent, or Firm—Hoffmann & Baron, LLP

[57] ABSTRACT

The invention relates to a charging method and a charging arrangement for a measuring system which measures the heart rate. The functional unit of the measuring system comprises at least a transmitter unit (100) and/or a receiver unit. The charging arrangement comprises a charging unit (340). The charging coil (320) of the charging unit is arranged to transfer electric energy inductively to the power source (302) of the functional unit (100) via an induction coil (310). The induction coil (130) of the functional unit (100) used for charging is connectable to more than one inductively active function in addition to charging.

15 Claims, 5 Drawing Sheets

CHARGING METHOD AND CHARGING ARRANGEMENT

FIELD OF THE INVENTION

The invention relates to a charging method particularly for a measuring system which measures the function of at least one organ from the user's body non-invasively and comprises at least one functional unit, such as a transmitter unit or a receiver unit, which comprises at least one induction coil for an inductively active function and a power source.

The invention also relates to a charging arrangement particularly for a measuring system, which is arranged to measure the function of at least one organ from the user's body non-invasively and which comprises at least one functional unit, such as a transmitter unit or a receiver unit, which comprises a power source and at least one induction coil for an inductively active function.

BACKGROUND OF THE INVENTION

Vital functions can be measured telemetrically using a non-invasive measuring device. An example of such a measuring device is a system which measures human heart rate and usually comprises several functional units, such as a transmitter unit, receiver unit and data transmission unit. Each functional unit usually comprises a battery which functions as the unit's power source. The transmitter unit means a unit which is provided with electrodes and is held against the human body, particularly against the chest. This unit is often implemented as a transmitter belt attached around the body. The receiver unit refers to a watch-like unit which is worn on the wrist, for example, and which telemetrically interacts with the transmitter unit on the basis of inductive activity. The data transmission unit, which communicates telemetrically with the receiver unit, is used for transmitting data collected in the receiver unit to a computer, for example. The computer can also be used for controlling both the transmitter and the receiver units via the data transmission unit.

Measurement of the heart rate is based on monitoring the function of the heart. When the heart muscle contracts, it causes a series of electric impulses which can be measured in the body. The measurement and analysis of this signal is known as electrocardiography (EKG). The signal itself is called an EKG signal. Different phases of the heart cycle can be discerned in the EKG signal. These are called P, Q, R, S, T and U waves. Sensors measuring height and water depth, for example, can be connected to the measuring system.

The power sources of the different functional units, which are typically batteries, are changed after the voltage level has decreased too much. This complicates the use of the device since even though the charge of a battery decreases in a known way, the fact that the electric energy of the power source has run out usually surprises the user e.g. in the middle of exercise.

The unit that receives the heart rate usually comprises a piezoelectric sound signalling device, electroluminescent light source and at least a receiver for the heart rate. For the function of each device the prior art solutions comprise a separate induction coil. Since the receiver unit, in particular, is typically a device similar to a wrist watch, the space needed for several coils constitutes a major problem. The use of several coils also raises the price of the device.

BRIEF DESCRIPTION OF THE INVENTION

The object of the invention is to provide a method and an arrangement implementing the method which eliminate the above-mentioned problems. This avoid problems caused by a decrease of the battery capacity and substantially reduces the need to change battery-like power sources. The number of coils required in the functional units can also be reduced, if necessary. This is achieved with the method formed in accordance with the present invention the method being characterized in that the measuring system comprises a charging unit and charging of the power source of at least one functional unit is performed wirelessly by means of an induction coil in such a manner that the charging coil of the charging unit transfers energy by means of interaction based on inductive activity to the power source of the functional unit via the induction coil of the functional unit; and the induction coil of the functional unit used for charging is connectable to more than one inductively active function in addition to charging.

The charging arrangement of the invention is characterized in that the charging arrangement comprises a charging unit and charging of the power source of at least one functional unit is performed wirelessly by means of an induction coil in such a manner that the charging coil of the charging unit is arranged to transfer energy by means of interaction based on inductive activity to the power source of the functional unit via the induction coil of the functional unit; and the induction coil of the functional unit used for charging is connectable to more than one inductively active function in addition to charging.

The charging method and charging arrangement according to the invention provide several advantages. The chargeable batteries of the functional units can be charged wirelessly which ensures that the power source to be charged functions in every situation. Furthermore, the size of the functional units can be kept small since the number of coils can be minimized.

BRIEF DESCRIPTION OF THE FIGURES

The invention will be described in greater detail by means of preferred embodiments with reference to the accompanying drawings, in which.

DETAILED DESCRIPTION OF THE INVENTION

The solution of the invention is particularly suitable for use in a measuring system which measures the heart pulse.

Figure 1:
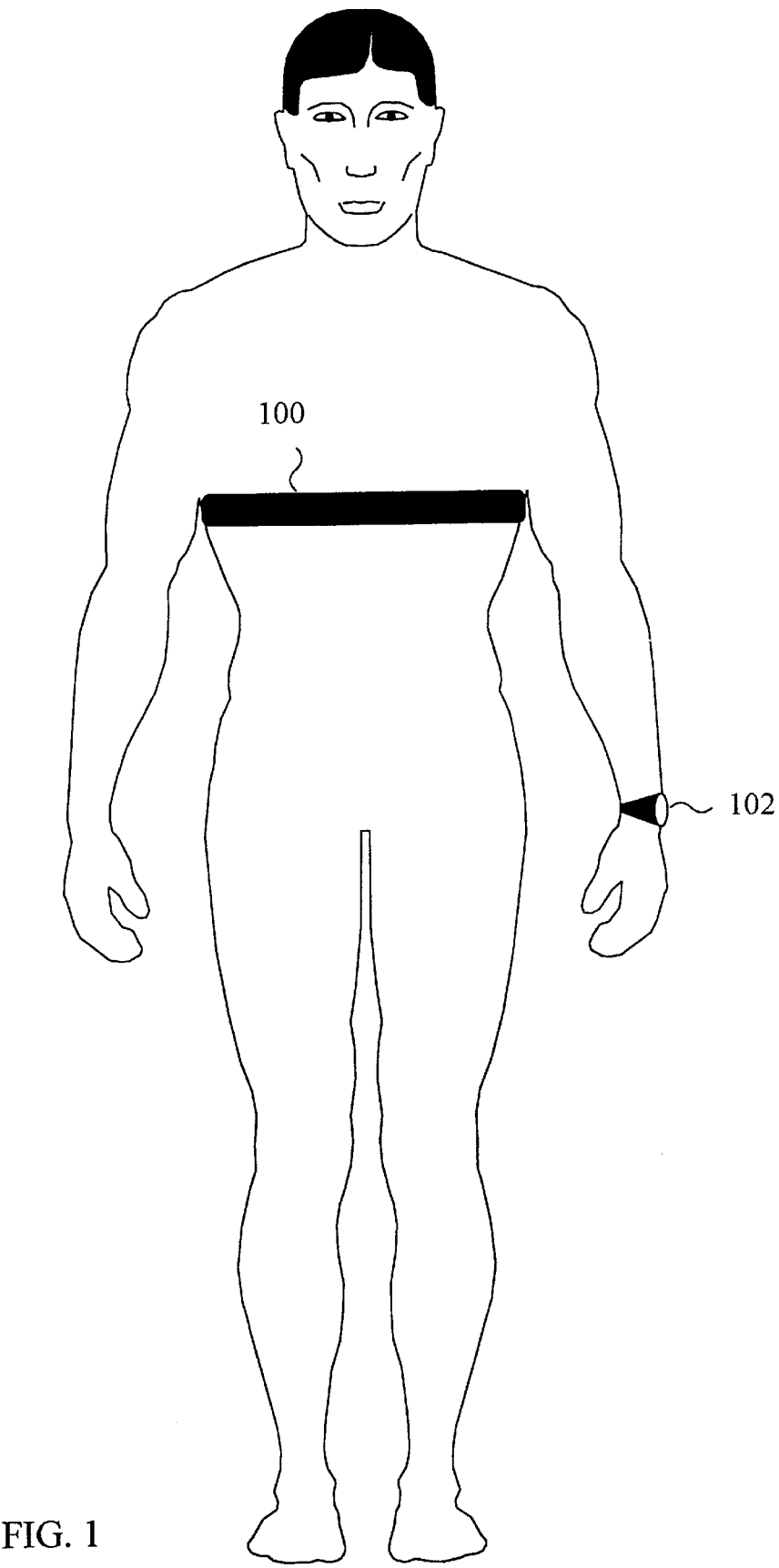
FIG. 1 illustrates a user who has a transmitter unit attached around his chest and a receiver unit on his wrist.

FIG. 1 illustrates a preferred embodiment of the present invention, i.e. a heart rate meter. The heart rate meter usually comprises several functional units, including a transmitter unit 100 which is attached around the user's chest and measures the heart rate, and a receiver unit 102 of the measuring system which the user wears on his wrist.

The measuring part, which comprises a transmitter unit and a receiver unit, may also have a one-piece structure in which case the heart rate meter is worn on the wrist and the heart rate is measured from the wrist. Using the modern technology a better measuring result is, however, achieved with a solution described above in which the measuring part is divided into two parts: a wireless transmitter unit 100 which measures the heart rate and is attached around the user's chest and a receiver unit 102 which the user wears on his wrist.

Figure 2A:
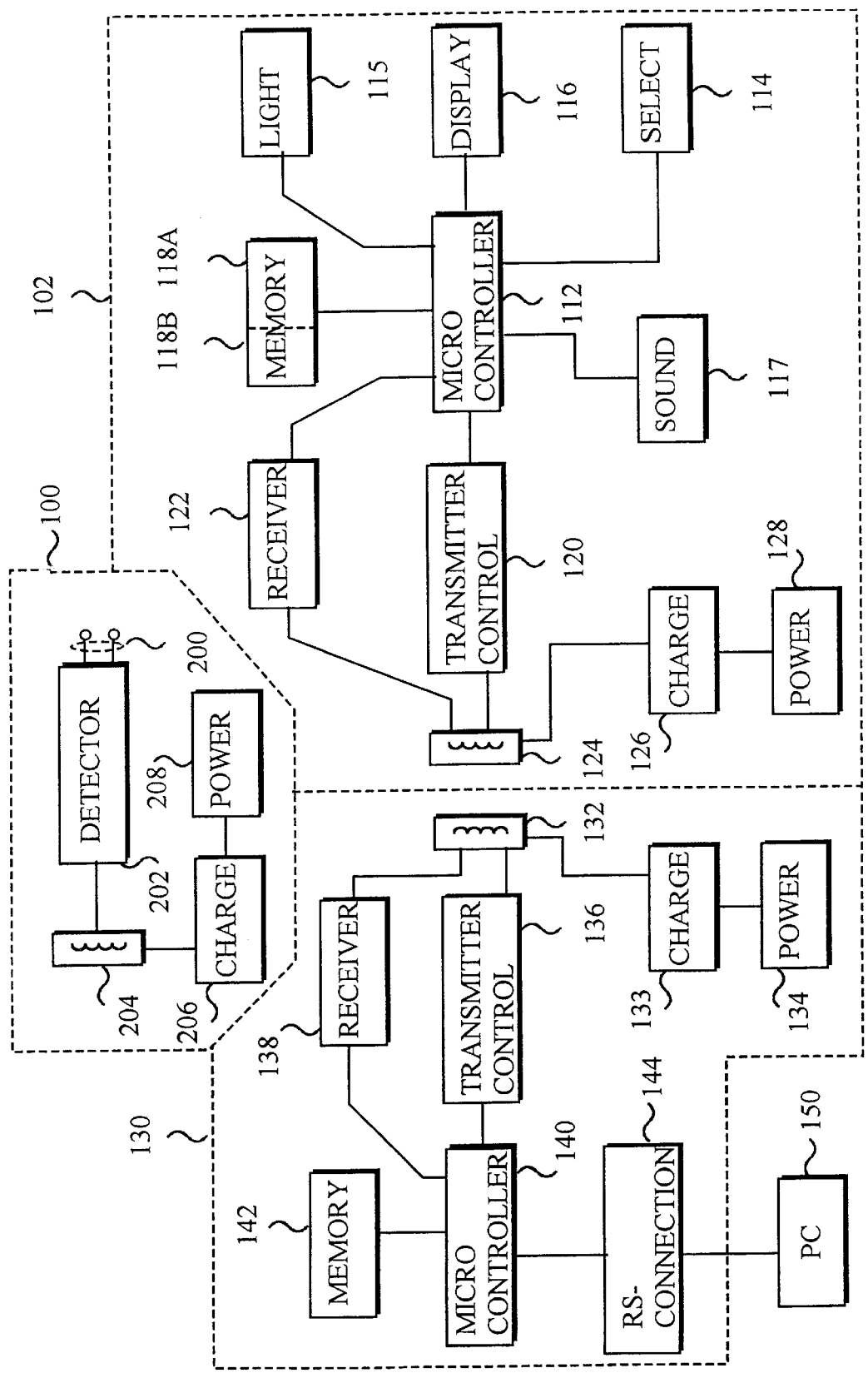
FIG. 2A is a block diagram illustrating a transmitter unit, receiver unit and data transmission unit.
Figure 2B:
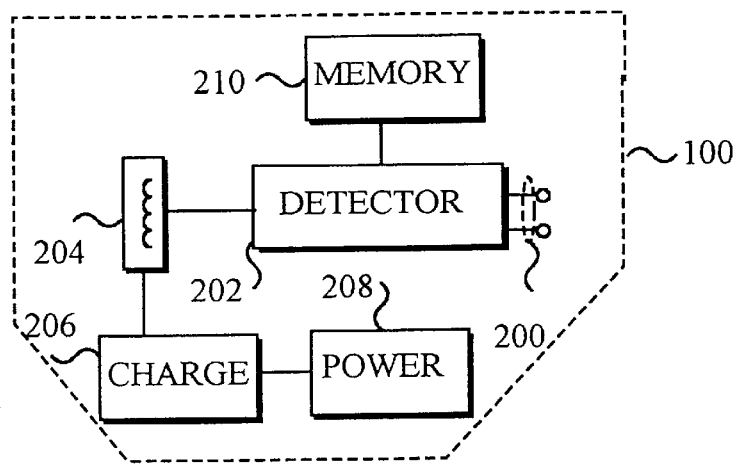
FIG. 2B illustrates a transmitter unit provided with a memory.
Figure 2C:
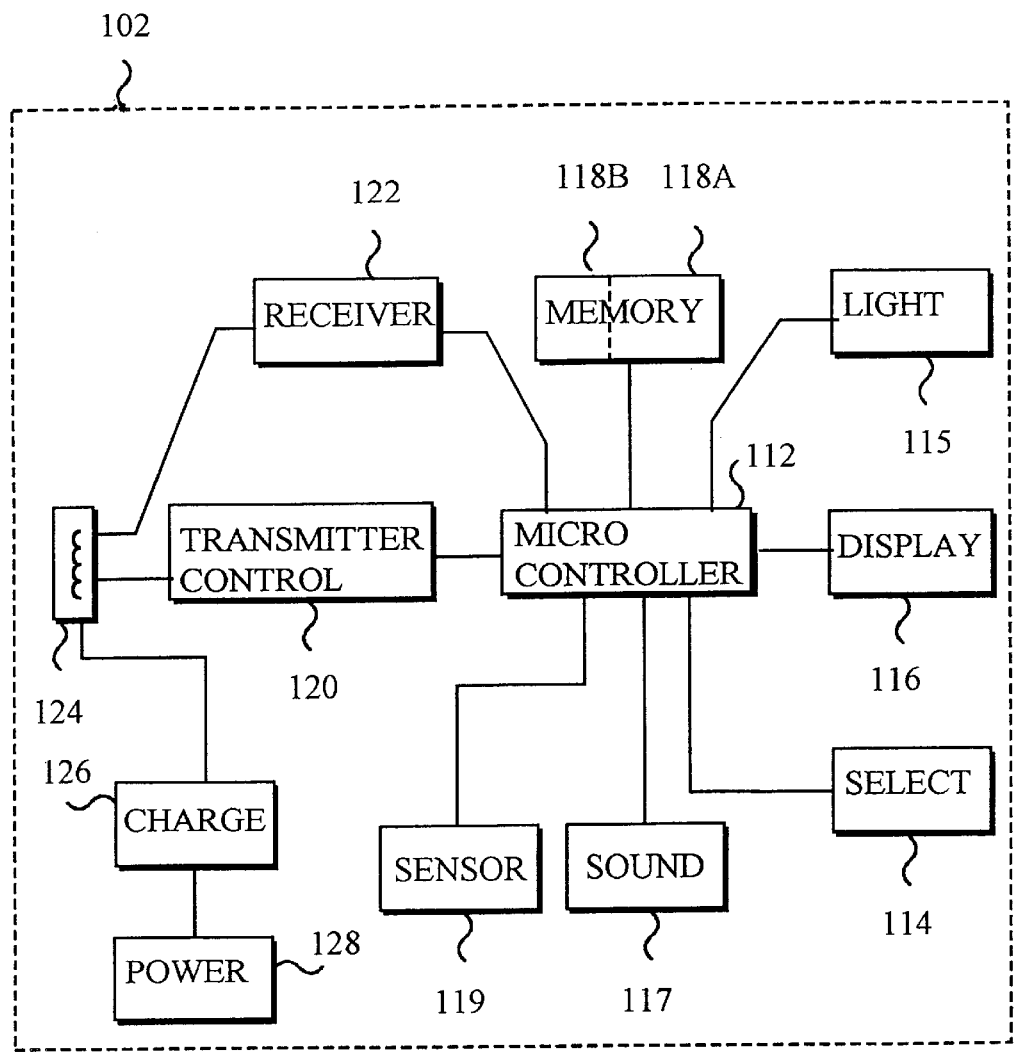
FIG. 2C illustrates a receiver unit provided with a sensor.

FIGS. 2A, 2B and 2C illustrate different systems which use telemetric data transmission for measuring the heart rate. The main parts of the system are a telemetric transmitter unit 100, telemetric receiver unit 102, data transmission unit 130 and data processing and controlling unit 150, which may be e.g. a PC. In the embodiment of FIGS. 2A and 2B a transmission unit 100 known per se can be used, the unit comprising EKG electrodes 200, a block 202 for pre-amplifying the EKG and detecting the pulse, inductance 204, charging block 206 and power source 208. The output received from the block 202 is a heart rate signal controlling the inductance, i.e. induction coil 204. The interval between the pulses of the heart rate signal, or between the pulse groups in encoded systems, is preferably the same as the interval between the heart beats. Thus a magnetic field alternating at the same rate as the heart rate is generated to the inductance 204, which inductively interacts, i.e. is inductively active, e.g. with the induction coil 124 of the receiver through the magnetic field. The power source 208 produces the electric power needed by each block of the transmitter unit 100 (for the sake of clarity the power supply wires are not illustrated in FIG. 2). In the inventive solution the power source 208 can be charged by transferring electric energy via the induction coil 204. The charging block 206 is responsible for disturbance-free charging.

As shown in FIGS. 2A and 2B, the transmitter unit 100 may also comprise a memory 210, in which case the transmitter unit 100 does not need to be paired with a receiver unit 102, but the transmitter unit 100 stores the measurement data in its memory 210 from which the measurement data are unloaded to a computer 150 for example via the data transmission unit 130 for processing and analysis.

The receiver unit 102 comprises a control part 112. The control part 112 also controls a user interface which comprises selection means 114 and display means 116. The selection means 114 is typically a keyboard by means of which the user employs the receiver unit 102. The display means 116, such as an LCD display, conveys visual information to the user. The receiver unit typically also comprises a light source 115 for illuminating the display 116 and a sound signalling device 117. The control part 112 is typically a microprocessor which comprises a ROM memory 118A in which the software controlling the device is stored. The device may also contain additional memory 118B in which the data gathered during the measuring can be stored, e.g. information on the heart rate, time and other user-specific parameters. The control part 112 may also be implemented by using an ASIC circuit or other electronic components. The receiver 102 further comprises a transmission controller 120, receiver means 122 and inductance 124. The transmission controller 120 generates data transmission from the receiver unit 102 to the data transmission unit 130 using the inductance 124. By means of the inductance 124 the receiver means 122 receive information in the form of induced voltage from the inductance 132 of the data transmission unit 130 and converts it to a digital form for the microprocessor 112. The inductance 124, such as a coil, is excited to resonance by means of a capacitor (not shown) using the frequency employed for data transmission. The receiver unit 102 also comprises a charging part 126 and a power source 128. The power source 128 feeds electric power into each block of the receiver unit 102 (for the sake of clarity the power supply wires are not illustrated in FIG. 2). In the inventive solution the power source 128 can be charged by transferring electric energy via the induction coil 124. The charging block 126 is responsible for disturbance-free charging.

The receiver unit 102, which is typically worn on the wrist like a watch, may also independently measure the user's heart rate or another vital function by means of sensors 119, as shown in FIG. 2C. The measuring can be performed optically and/or with a pressure sensor according to the prior art. In that case the receiver unit 102 substantially functions both as the receiver 102 and as the transmitter 100, i.e. a separate transmitter unit 100 is not a necessary part of the measuring system.

The data transmission unit 130 comprises an inductance 132, transmission controller 136, reception means 138, computing unit such as a microprocessor 140, memory 142 and interface 144. The data transmission unit 130 communicates with the data processing unit 150, such as a PC, via the interface 144. The inductance 132 of the data transmission unit 130 is at the same resonance frequency as the inductance 124 of the receiver unit. The purpose of the transmission controller 136 is to generate a control signal for the inductance 132. The purpose of the receiver means 138 is to receive incoming serial data from the inductance 124 via the inductance 132. The microprocessor 140 converts the transmitted data to a suitable form for the PC (data processing unit 150). The memory 142 of the data transmission unit 130 may store files that have been read, if necessary. The interface 144, such as RS232, converts the voltage levels of the interface to suit the interface that is used. The power source 134 feeds electric power into each block of the data transmission unit 130 (for the sake of clarity the power supply wires are not illustrated in FIG. 2). In the inventive solution the power source 134 can be charged by transferring electric energy via the induction coil 132. The charging block 133 is responsible for disturbance-free charging.

Charging will now be described in greater detail with reference to FIG. 3, where the transmitter unit 100 is being charged. Instead of the transmitter unit, any other functional unit of the measuring system can be charged in the same way. The charging device 340 comprises a coil 320, transistor 322, capacitor 324 and oscillator 326. The charging device 340 is preferably always functioning and thus the oscillator 326 resonates. Electric resonance drives the transistor 322 alternately to a conducting state and alternately to a non-conducting state, in which case the collector current of the transistor 322 also tends to resonate in the same way because the collector is connected to operating voltage VCC via the coil 320. The voltage at the transistor's 322 collector also alternates at the rate of the resonance. When a unit of the measuring system is set to be charged, the coil 320 interacts inductively with another coil. Thus the pulse form also changes due to the change of the resonance circuit and the amplitude of resonance decreases at the transistor's 322 collector. A pair consisting of a diode 328 and a capacitor 330 functions as the detector of the maximum value of the collector voltage.

In a preferred embodiment of the invention the charging device 340 comprises a charging detector circuit 323, which in turn comprises for example the diode 328, capacitor 330, voltage reference source 332, comparator 334, LED 336 and resistance 338. When operating voltage is switched to the charging device 340, it begins to operate. This switching functions so that the LED 336 does not emit light when the charging device 340 is not charging. This results from the fact that the input voltage to the positive input pole (+) is higher than the input voltage to the negative input pole (−) of the comparator 334 from the voltage reference source 332. In that case the output voltage of the comparator 334 is positive. The diode 328 and capacitor 330 function as detectors of the maximum value of the collector voltage, which is compared with the voltage reference. When the functional unit is charged, the mutual inductance between the charging coil 320 and the inductance coil 310 changes, and thus the amplitude of the transistor's 322 collector voltage decreases, and furthermore, after the detector of the maximum value, the input voltage to the positive input pole (+) of the comparator 334 is lower than the voltage of the voltage reference source 332. Since the voltage of the negative input pole (−) of the comparator 334 is now higher, the output voltage of the comparator 334 decreases and electric power flows from the operating voltage VCC through the resistance 338 and LED 336, in which case the LED 336 emits light, thus indicating to the user that charging is going on. The light of the LED 336 indicating charging preferably goes out if the functional unit is disconnected from charging before the charging has finished or the charging unit is switched off.

Figure 3:
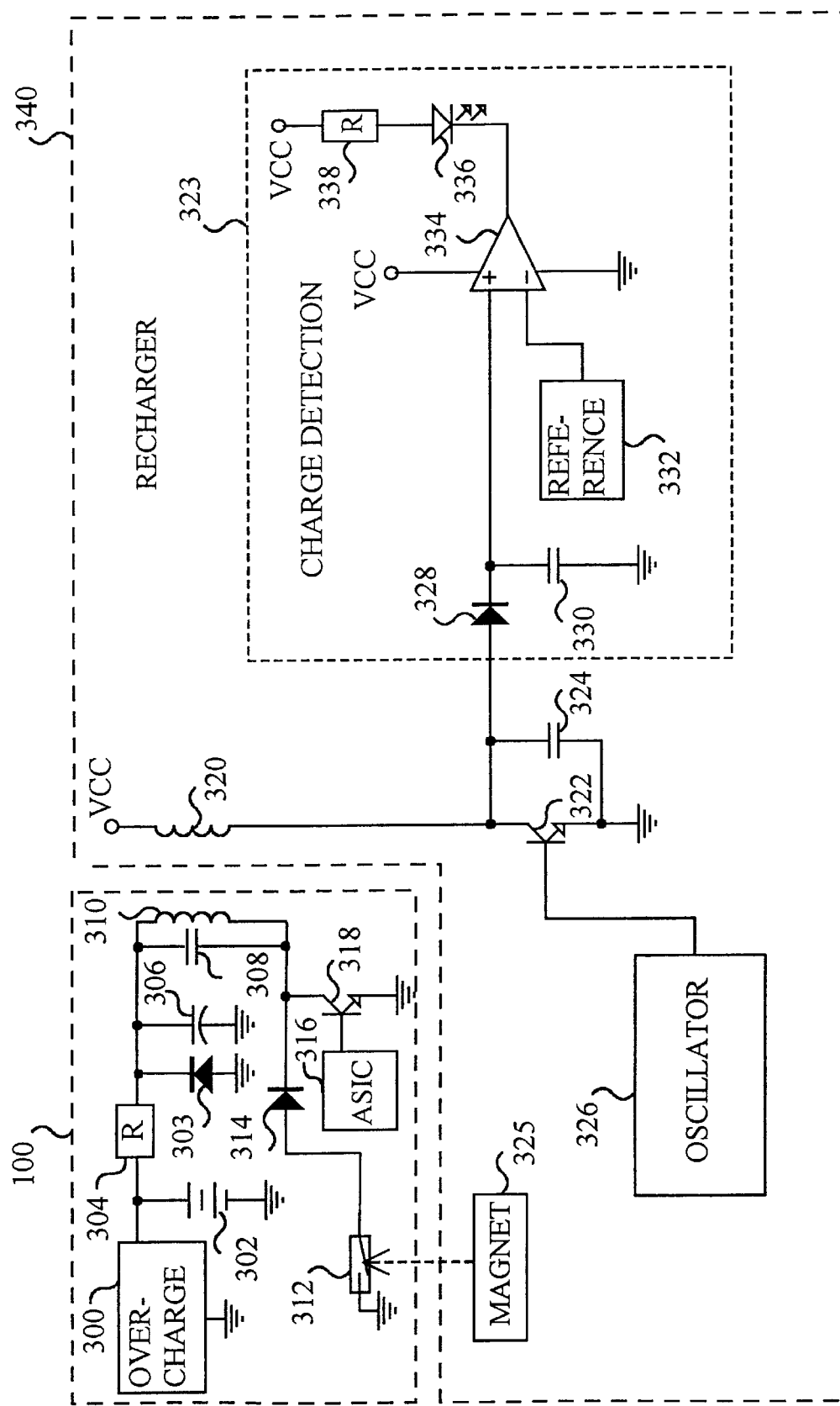
FIG. 3 illustrates charging of the transmitter unit at a general level.

When the transmitter unit 100, for example, is charged as illustrated in FIG. 3, the charging coil 320 transfers electric energy to the induction coil 310 by means of inductive interaction, and the coil 310 forms a resonance circuit with the capacitor 308. Charging is preferably activated by the magnet 325 of the charging device 340 which closes a relay 312 of the functional unit so that one end of the induction coil 310 connects to the ground. Charging can also be activated by using another kind of switching arrangement obvious to a person skilled in the art. In FIG. 3 one end of the charging coil 310 is connected to the ground via a diode 314. The electric energy transferred to the induction coil 310 is transferred to the battery 302 to be charged. The transmitter unit 100, like other chargeable functional units, preferably comprises a suppression block 300 of excess charge, i.e. overvoltage, the implementation of the block being obvious to a person skilled in the art. There are several different electric suppression circuits of overvoltage, but the simplest solution is for example a zener diode. The suppression block 300 of overvoltage protects the power source 302, which is a chargeable battery, against excessive charging voltages. The block 300 and relay 312 are examples of parts that the charging blocks 126, 133 and 206 of FIG. 2 may comprise. The resistance 304, for example, limits the charging current. The diode 303 enables charging of the battery 302 with the input alternating current received from the induction coil 310. The charging capacitor 306, which functions for example in filtering, is a rather irrelevant component in charging like the ASIC circuit 316 and switching block 318, which in this example is a transistor, but could also be for example a darlington pair in equivalent switching. These components are, however, irrelevant to the invention. After charging the transmitter unit 100 functions as the transmitter of pulse information by means of the induction coil 310. In addition to charging, the induction coil of the functional unit used for charging is connectable to more than one inductive interaction. The induction coil preferably participates in only one interaction at a time.

Figure 4:
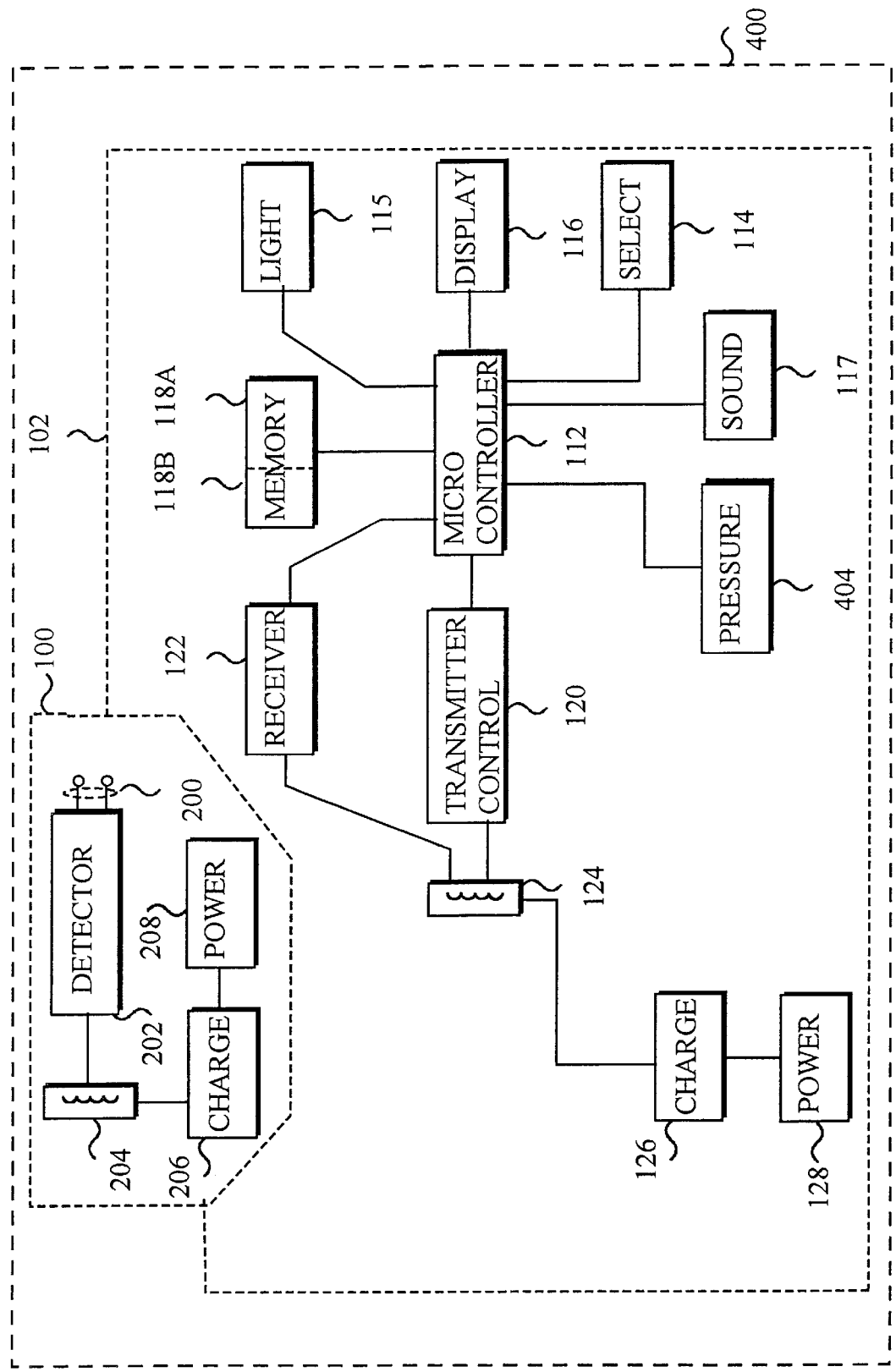
FIG. 4 illustrates a diving instrument.

As shown in FIG. 4, the functional unit to be charged may also be a diving instrument 400 which comprises a transmitter unit 100 and a receiver unit 102. The diving instrument may also be only a transmitter part 100 provided with a memory 210 as shown in FIG. 2B, or a receiver unit 102 provided with a sensor 404 for measuring the pressure as shown in FIG. 4. When the user is diving, the diving instrument measures, in addition to the heart rate, the water pressure by means of the sensor 404 for determining the depth. The diving instrument may also determine how much nitrogen is absorbed into the user's tissues. FIG. 4 illustrates a block diagram of the diving instrument.

The induction coil which the functional units employ for receiving charging energy may be the same coil the functional units use for telemetric data transmission or for another internal function which requires inductive activity, such as sound signalling or illumination of the display. The sound signalling component is typically a piezoelectric crystal, and the resonance frequency needed for controlling it is generated by means of the coil and capacitor in a known manner. In this resonance circuit the induction coil to be used for charging may function as the required inductance. The display can be illuminated for example with a light source which is based on electroluminescence and whose controlling according to the prior art requires an AC voltage of at least several dozens of volts. This AC voltage is generated from the direct voltage of the power source preferably in a prior art manner using an inductive coil, which in the inventive solution is the induction coil used for charging. This prior art solution is disclosed for example in U.S. Pat. No. 4,527,096 which is hereby incorporated by reference. In the solution according to U.S. Pat. No. 4,527,096 the IC circuit uses the coil for producing the AC voltage required by the electroluminescence component. The components used in the inventive solution are conventional prior art electronic, optoelectronic or mechanical components which are obvious to a person skilled in the art.

Even though the invention has been described with reference to the example according to the accompanying drawings, it is clear that the invention is not restricted to it, but may be varied in several ways within the scope of the inventive concept disclosed in the appended claims.

What is claimed is:

1. A charging method particularly for a measuring system which measures the function of at least one organ from a user's body non-invasively and comprises at least one functional unit, the at least one functional unit comprising at least one induction coil which performs an inductively active function and a power source, wherein the measuring system comprises a charging unit and the charging unit comprises a charging coil, charging of the power source of the at least one functional unit being performed wirelessly by the induction coil, the charging coil of the charging unit transferring energy by interaction based on inductive activity to the power source of the functional unit via the induction coil of the functional unit; and the induction coil of the functional unit used for charging being connectable to more than one inductively active function in addition to charging.

2. A method according to claim 1, wherein the induction coil participates in only one inductively active function at a time.

3. A method according to claim 1, wherein the functional unit to be charged is a transmitter unit.

4. A method according to claim 1, wherein the measuring system comprises a receiver unit and the functional unit to be charged is the receiver unit.

5. A method according to claim 1, wherein the functional unit to be charged is a diving instrument.

6. A method according to claim 1, wherein the induction coil of the functional unit used for charging can be used for at least one of the following inductive functions in addition to charging: inductive interaction between a plurality of functional units, generation of a sound signal and generation of a background light of a display.

7. A method according to claim 1, wherein the measuring system further comprises a data transmission unit, the data transmission unit comprising a second induction coil, the data transmission unit interacting inductively with at least one of a receiver unit and a transmitter unit via the second induction coil.

8. A charging arrangement particularly for a measuring system which is arranged to measure the function of at least one organ from a user's body non-invasively and comprises at least one functional unit, the at least one functional unit comprising at least one induction coil which performs an inductively active function and a power source, wherein the charging arrangement comprises a charging unit and the charging unit comprises a charging coil, charging of the power source of the at least one functional unit being performed wirelessly by the induction coil, the charging coil of the charging unit transferring energy by interaction based on inductive activity to the power source of the functional unit via the induction coil of the functional unit; and the induction coil of the functional unit used for charging being connectable to more than one inductively active function in addition to charging.

9. An arrangement according to claim 8, wherein the induction coil participates in only one inductively active function at a time.

10. An arrangement according to claim 8, wherein the functional unit to be charged is a transmitter unit.

11. An arrangement according to claim 8, wherein the measuring system comprises a receiver unit and the functional unit to be charged is the receiver unit.

12. An arrangement according to claim 8, wherein the functional unit to be charged is a diving instrument.

13. An arrangement according to claim 8, wherein the induction coil of the functional unit used for charging can be used for inductively active interaction between two functional units in addition to charging.

14. An arrangement according to claim 8, wherein, if the functional unit comprises at least one of sound signalling and a background light of a display, the induction coil of the functional unit used for charging can be used for at least one of the following functions in addition to charging: generation of a sound signal and generation of the background light of the display.

15. An arrangement according to claim 8, wherein the measuring system further comprises a data transmission unit, the data transmission unit comprising a second induction coil, the data transmission unit interacting inductively with at least one of a receiver unit and a transmitter unit via the second induction coil.

* * * * *